US009512379B2

(12) United States Patent
Seddon et al.

(10) Patent No.: US 9,512,379 B2
(45) Date of Patent: Dec. 6, 2016

(54) OVERBASED FRICTION MODIFIERS AND METHODS OF USE THEREOF

(75) Inventors: Elisa J. Seddon, Lyndhurst, OH (US); Daniel J. Saccomando, Sheffield (GB); Richard J. Vickerman, Stow, OH (US); Jason R. Brown, Katy, TX (US); Mohamed G. Fahmy, Eastlake, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 370 days.

(21) Appl. No.: 14/233,397

(22) PCT Filed: Jul. 19, 2012

(86) PCT No.: PCT/US2012/047301
§ 371 (c)(1),
(2), (4) Date: Jan. 17, 2014

(87) PCT Pub. No.: WO2013/012987
PCT Pub. Date: Jan. 24, 2013

(65) Prior Publication Data
US 2014/0179574 A1  Jun. 26, 2014

Related U.S. Application Data

(60) Provisional application No. 61/510,227, filed on Jul. 21, 2011.

(51) Int. Cl.
| *C10M 133/02* | (2006.01) |
| *C10M 133/34* | (2006.01) |
| *C07D 295/00* | (2006.01) |
| *C10M 133/44* | (2006.01) |
| *C07D 207/277* | (2006.01) |
| *C10M 159/20* | (2006.01) |

(52) U.S. Cl.
CPC ........ *C10M 133/44* (2013.01); *C07D 207/277* (2013.01); *C10M 159/20* (2013.01); *C10M 2215/04* (2013.01); *C10M 2219/106* (2013.01); *C10N 2210/02* (2013.01); *C10N 2230/06* (2013.01); *C10N 2240/042* (2013.01); *C10N 2240/044* (2013.01); *C10N 2240/08* (2013.01); *C10N 2240/10* (2013.01)

(58) Field of Classification Search
CPC .................... C10M 2217/06; C10M 2217/028; C07D 207/34
USPC ........................................ 508/297; 548/531
See application file for complete search history.

(56) References Cited

U.S. PATENT DOCUMENTS

| 2,604,449 | A | | 7/1952 | Bryant et al. | |
| 2,757,125 | A | | 7/1956 | Mudrak et al. | |
| 2,868,628 | A | * | 1/1959 | Chenicek | C10L 1/2222 252/403 |
| 2,936,309 | A | * | 5/1960 | Bavley | C07D 207/277 524/104 |
| 3,218,264 | A | * | 11/1965 | Katz | C07D 207/277 252/392 |
| 3,224,975 | A | | 12/1965 | Hinkamp et al. | |
| 4,070,370 | A | * | 1/1978 | Elliott | C07D 207/277 508/268 |
| 4,512,903 | A | | 4/1985 | Schlicht et al. | |
| 4,581,364 | A | * | 4/1986 | Weber | C07D 207/26 514/343 |
| 4,886,612 | A | | 12/1989 | Higaki et al. | |
| 5,750,476 | A | | 5/1998 | Nibert et al. | |
| 5,858,929 | A | | 1/1999 | Sumiejski et al. | |
| 2013/0152314 | A1 | * | 6/2013 | Sabelle | C07D 207/277 8/426 |

(Continued)

FOREIGN PATENT DOCUMENTS

DE  102009030412 A1  12/2010
EP  0976813 A1  2/2000

(Continued)

OTHER PUBLICATIONS

Beresnevicius et al.: "Reactions of aminoquinolines with unsaturated carboxylic acids. 4. synthesis of 4-carboxy-1-quinolyl-2-pyrrolidinones", Chemistry of Heterocyclic Compounds, vol. 36, No. 7, Jan. 1, 2000, pp. 818, 821.
Paytash et al.: "Reaction of itaconic acid with primary amines", J. Am. Chem. Soc., vol. 72, No. 3, 1950, pp. 1415-1416.
O'Connor et al.: "Overbased Lubricant Detergents—a Comparative Study", Lubrication Science, vol. 6, No. 4, 1994, pp. 297-325.
Delfort et al.: "Functionalization of overbased calcium sulfonates synthesis and evaluation of antiwear and extreme pressure performances", Lubrication Engineering, vol. 51, No. 12, 1995, pp. 981-990.

*Primary Examiner* — Vishal Vasisth
(74) *Attorney, Agent, or Firm* — Christopher P. Demas; Teresan W. Gilbert

(57) ABSTRACT

The present invention provides a multipurpose overbased metal salt of the reaction product of a hydrocarbyl substituted amine with an itaconate, such as an N-substituted 4-carboxypyrrolidin-2-one, and methods of employing the same in lubricating compositions. Overbasing the N-substituted 4-carboxypyrrolidin-2-one can provide improved friction modifying performance to the compound as well as impart multi-functionality to the compound, i.e., the compound may function as a friction modifier as well as, for example, a detergent, anti-wear or extreme pressure agent and dispersant in lubricating compositions. The lubricating compositions containing the overbased N-substituted 4-carboxypyrrolidin-2-one are preferably intended to be employed in a method for lubricating a mechanical device, such as an automatic or manual transmission. However, it is envisioned that the compound can be employed in engine oil lubricants and any other type of functional fluid.

11 Claims, No Drawings

(56) References Cited

U.S. PATENT DOCUMENTS

2013/0217892 A1* 8/2013 Wacker ............... A01N 25/02
548/531

FOREIGN PATENT DOCUMENTS

| GB | 1323061 A | 7/1973 |
|---|---|---|
| WO | 2004/007652 A1 | 1/2004 |

* cited by examiner

OVERBASED FRICTION MODIFIERS AND METHODS OF USE THEREOF

This application is a 371 of PCT/US12/47301, filed Jul. 19, 2012 which claims benefit of 61/510,227, filed Jul. 21, 2011.

BACKGROUND OF THE INVENTION

The present invention relates to the field of additives for fluids such as automatic transmission fluids (ATF), manual transmission fluids (MTF), traction fluids, fluids for continuously variable transmission fluids (CVTs), dual clutch automatic transmission fluids, farm tractor fluids, and engine lubricants, as well as additives for engine oil.

In the automatic transmission marketplace, where there is rapid engineering change driven by the desire to reduce weight and increase transmission torque capacity, there is a desire for automatic transmission fluids that exhibit a high static coefficient of friction for improved clutch holding and launch capacity. Continuously slipping torque converter clutches and launch clutches, for instance, impose exacting friction requirements on automatic transmission fluids (ATFs). The fluid must have a good friction versus sliding speed relationship, or an objectionable phenomenon called shudder will occur in the vehicle. Transmission shudder is a self-excited vibrational state commonly called "stick-slip" or "dynamic frictional vibration" generally occurring in slipping torque converter clutches. The friction characteristics of the fluid and material system, combined with the mechanical design and controls of the transmission, determine the susceptibility of the transmission to shudder. Plotting the measured coefficient of friction ($\mu$) versus sliding speed (V), commonly called a $\mu$-V curve, has been shown to correlate to transmission shudder. Both theory and experiments support the region of positive to slightly negative slope of this $\mu$-V curve to correlate to good anti-shudder performance of transmission fluids. A fluid which allows the vehicle to operate without vibration or shudder is said to have good "anti-shudder" performance. The fluid should maintain those characteristics over its service lifetime. The longevity of the anti-shudder performance in the vehicle is commonly referred to as "anti-shudder durability". The variable speed friction tester (VSFT) measures the coefficient of friction with respect to sliding speed simulating the speeds, loads, and friction materials found in transmission clutches and correlates to the performance found in actual use. The procedures are well documented in the literature; see for example Society of Automotive Engineers publication #941883.

The combined requirements of high static coefficient of friction and durable positive slope are often incompatible with traditional ATF friction modifier technology which is extremely well described in the patent literature. Many of the commonly used friction modifiers result in a low static coefficient of friction and are not durable enough on positive slope to be of sufficient use.

For manual transmissions, the synchronizer is one of the more important components of any manual gearbox. Increasing performance, reducing shift force (raising shift quality) and minimizing the between-the-gears energy losses are the primary objectives for a new generation of synchronizer systems. Improvements in the capacity of the brass system and the introduction of formed sintered cones are allowing economical re-engineering of existing synchronizer designs into more efficient designs (see Hoerbiger and Co. Engineering Report 32). Synchronizer materials are becoming more diverse to include materials such as carbon. This may include a range of substrates from graphite, or sintered graphite, materials through to carbon fibre woven or paper type materials. The frictional appetites of these systems can vary and hence friction modifiers selection can be critical. The chemistry of manual transmission lubricating oils needs to be reformulated for these designs to be able to maintain adequate friction in the synchronizer system and protect these parts from wear.

Many of the commonly used friction modifiers result in a low static coefficient of friction and do not have sufficient durability to be of practical use. Traditionally, detergents (the overbased metal salts of organic acids, such as sulfonates, phenates or salicylates and the like) have been used in ATF and MTF formulations. Further, conventional gear oils or manual transmission oils typically contain chemical components, such as active sulfur and surface-active amine organophosphates. While excellent as additives to provide extreme pressure lubrication, in the usual amounts these additives alone give rise to too large a decrease in friction, while also inadequately protecting friction surfaces from abrasive or corrosive wear. While such additives bring benefits to the overall formulation, they add to the complexity of the lubricant formulation in addition to adding cost. Many friction modifiers can be of limited solubility when in an additive package and thus it is beneficial for a highly soluble friction modifier, while maintaining or bettering its friction modifying and antiwear benefits.

There are patents, for example, U.S. Pat. No. 5,750,476, Nibert et al., May 12, 1998, where a type of friction modifier technology used to achieve this performance is described.

Additional patent literature describing technology for retaining positive $\mu$/v or anti-shudder characteristics include U.S. Pat. No. 5,858,929, Sumiejski et al., Jan. 12, 1999. These may employ metal detergents and combinations of friction modifiers.

Teqjui et al. in EP 0976813 disclose high synchromesh durability performance and gear protection of a manual transmission gearbox. Metal detergents are presented as a required component as overbased salicylates and a calcium sulfonate is shown in the comparative examples.

U.S. Pat. No. 4,512,903, Schlicht et al., Apr. 23, 1985, discloses amides prepared from mono- or poly-hydroxy-substituted aliphatic monocarboxylic acids and primary or secondary amines, useful as friction reducing agents.

PCT Publication WO04/007652, Adams et al., Jan. 22, 2004, discloses a fluid composition of (a) a friction modifier derived from the reaction of a carboxylic acid with an amino alcohol, the friction modifier containing at least two hydrocarbyl groups, and (b) a dispersant, which provides good friction properties in an automatic transmission.

U.S. Pat. No. 4,886,612, Higaki et al., Dec. 12, 1989, discloses a lubricating oil comprising at least one of various products, which can be various imidazolines or an oxazoline of the structure:

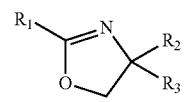

where $R_2$ and $R_3$ each represent $CH_2OCOR_1$, $CH_2OH$ or H, prepared by the condensation of a carboxylic acid (or a reactive equivalent thereof) with an amino alcohol; for example, the condensation of two moles of isostearic acid with one mole of tris-hydroxymethylaminomethane (THAM).

In addition, there is a desire to produce friction modifying compounds that are environmentally friendly and that can mitigate the effect of co-additives. Many lubricating fluids, such as engine oils and gear oils, contain a complex mixture of additives employed for various purposes. For example, most formulations require detergents to keep the formulation clean, anti-wear additives to protect against component wear, dispersants to provide increased solubility and so on. Some of these additives decompose into materials that may damage engine components and/or exhaust after-treatment devices. In addition, with respect to detergents in particular, the performance of current friction modifiers tends to be highly dependent on the structure of the organic portion of the detergent. Likewise, some co-additives, such as, for example, detergents, can cause long-term wear to mechanical components.

Thus, there is an interest not only in improving the performance of friction modifying compounds, but also making environmentally friendly friction modifiers that can mitigate the effects of co-additives in lubricant formulations.

SUMMARY OF INVENTION

The present invention provides a method for improving the friction modifying performance of a carboxylic pyrrolidinone compound while imparting multi-functionality and improved friction modifying performance by overbasing the compound. The inventors of this invention have discovered overbased salts of the reaction product of an itaconate and an amine that exhibit improved friction modifying performance, which provides durable friction control, and are more environmentally friendly (i.e. lower amounts of materials that may damage engine components and/or exhaust after-treatment devices) than some traditional friction modifiers, and that exhibit multi-functionality.

Thus, in one embodiment, the present invention provides an overbased salt of the reaction product of a hydrocarbyl substituted amine with an itaconate.

In another embodiment, there is provided an overbased metal salt of an N-substituted 4-carboxypyrrolidin-2-one, wherein the N-substituent comprises a hydrocarbyl group or a heteroatom-containing hydrocarbyl group having at least about 8 to about 60 carbon atoms, and esters or salts thereof.

The present invention also provides a lubricant composition comprising a major amount of an oil of lubricating viscosity and an overbased salt of an N-substituted 4-carboxypyrrolidin-2-one.

The present invention further provides a method for lubricating a mechanical device, comprising supplying thereto either of the above compositions.

DETAILED DESCRIPTION OF THE INVENTION

Various preferred features and embodiments will be described below by way of non-limiting illustration.

In one embodiment, the present invention provides an overbased metal salt of the reaction product of a hydrocarbyl substituted amine with an itaconate.

As used herein, the term "hydrocarbyl group" or "hydrocarbyl substituent" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(i) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulphoxy);

(iii) hetero substituents, that is, substituents which, while having a predominantly hydrocarbon character, in the context of this invention, contain other than carbon in a ring or chain otherwise composed of carbon atoms, and encompass substituents as pyridyl, furyl, thienyl and imidazolyl; and (iv) heteroatoms, including sulfur, oxygen, and nitrogen. In general, no more than two, preferably no more than one, non-hydrocarbon substituent will be present for every ten carbon atoms in the hydrocarbyl group; typically, there will be no non-hydrocarbon substituents in the hydrocarbyl group.

In certain embodiments, the hydrocarbyl substituted amine may comprise a mixture of individual groups on the same or different molecules having a variety of carbon numbers falling generally within the range of 8 to 22 or 12 to 22 or 8 to 20 or 12 to 20 carbon atoms, although molecules with hydrocarbyl groups falling outside this range may also be present, such as from 8 to 24, 8 to 32 or even 8 to 60 carbon atoms. If a mixture of hydrocarbyl groups is present, they may be primarily of even carbon number (e.g., 12, 14, 16, 18, 20, or 22) as is characteristic of groups derived from many naturally-occurring materials, or they may be a mixture of even and odd carbon numbers or, alternatively, an odd carbon number or a mixture of odd numbers. They may be branched, linear, or cyclic and may be saturated or unsaturated, or combinations thereof.

Suitable hydrocarbyl substituted amines include those, for example, in the Duomeen™, Triameen™, and Tetrameen™ series, available from Akzo, having a general structures such as

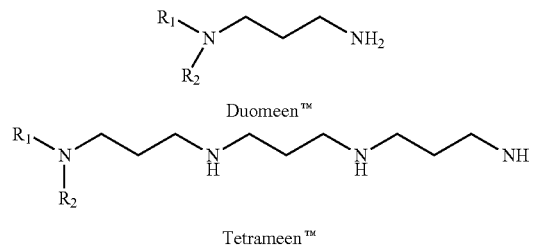

Duomeen™

Tetrameen™

Such polyamines may be prepared, for example, by the addition of the monoamine $R_1R_2NH$ to acrylonitrile, to prepare the alkyl nitrile amine (cyanoalkyl amine),

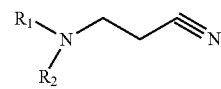

followed by catalytic reduction of the nitrile group using, e.g., $H_2$ over Pd/C catalyst, to give the diamine where at least one of $R_1$ and $R_2$ can be hydrogen or a hydrocarbyl group as defined above.

In certain embodiments the $R_1$ and $R_2$ hydrocarbyl groups may contain 16 to 18 carbon atoms, and sometimes predominantly 16 or predominantly 18, but up to 8 to 24, 8 to 32 or even 8 to 60 carbon atoms. In certain embodiments, the hydrocarbyl substituted amine may be in the form of a salt. Specific examples of $R_1$ and $R_2$ include mixed "coco" groups from cocoamine (predominantly $C_{12}$ and $C_{14}$ amines) and mixed "tallow" groups from tallowamine (predominantly $C_{16}$ and $C_{18}$ groups), isostearyl groups, and 2-ethylhexyl groups.

The itaconate can have the formula:

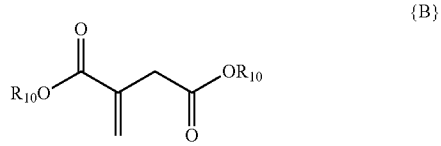

{B} where $R_{10}$ can be a hydrocarbyl groups as defined above, or hydrogen. Typically the $R_{10}$ itaconate is hydrogen or methyl, and the itaconate is 2-methylene succinic acid or dimethyl itaconate.

In one embodiment, the reaction product of a hydrocarbyl substituted amine with an itaconate provides an N-substituted 4-carboxypyrrolidin-2-one.

In one example embodiment, an N-substituted 4-carboxypyrrolidin-2-one can be produced by the reaction of oleylamine with dimethyl itaconate.

In a further embodiment, N-substituted 4-carboxypyrrolidin-2-one can be produced by the reaction product of dimethyl itaconate with Duomeen 2HT™, where $R_1$ and $R_2$ are both hydrogenated tallow; of dimethyl itaconate with Duomeen 2C™, where $R_1$ and $R_2$ are both coco; and of dimethyl itaconate with a Duomeen™ wherein $R_1$ and $R_2$ are different, for example, where $R_1$ is tallow and $R_2$ is 2-ethylhexyl.

In another example embodiment, an N-substituted 4-carboxypyrrolidin-2-one can be the reaction product of dimethyl itaconate with a Tetrameen™, wherein $R_1$ is tallow and $R_2$ is hydrogen. In further embodiments, the itaconate/Tetrameen™ reaction product may be salted with a triazole or a derivative thereof, such as, for example, dimercaptothiadiazole. Likewise, any of the other reaction products may be salted.

The N-substituted 4-carboxypyrrolidin-2-one can be produced, in one embodiment, by the reaction of an amine hydrocarbyl group with an itaconate in a suitable solvent, such as methanol, to produce an N-substituted 4-carboxypyrrolidin-2-one, followed by optional salt formation and/or stripping of the itaconate $R_{10}$—, for example, as a saponified ester, and then overbasing.

Overbased compositions can be prepared by reacting a mixture comprising an acidic organic compound, such as that of the reaction product of a hydrocarbyl substituted amine with an itaconate, a reaction medium comprising at least one inert, organic solvent for the organic anionic compound, a basic metal compound, typically a metal hydroxide or oxide, and a promoter. Generally, the basic metal compounds are oxides, hydroxides, chlorides, carbonates, and phosphorus acids (phosphonic or phosphoric acid) salts or partial esters, and sulfur acid (sulfuric or sulfonic) salts or partial esters (except sulfonic). The metals are generally alkali, alkaline earth, and transition metals. Examples of the metals of the basic metal compound include sodium, potassium, lithium, magnesium, calcium, barium, titanium, manganese, cobalt, nickel, copper, zinc, and preferably sodium, potassium, calcium, and magnesium. In one embodiment, the metal salts are prepared by reacting water with a mixture comprising an organic anionic compound, a reaction medium and a promoter. These metal salts and methods of making the same are described in U.S. Pat. No. 4,627,928. The basic metal compound can be added during the process of overbasing the hydrocarbyl substituted amine/itaconate reaction product to give a product having a total base number (TBN) of between 50 and 1000, or 100 and 800, or 150 and 600, or 250 and 500 on an active basis, i.e., on an oil free basis. The TBN refers to the amount of acid (perchloric or hydrochloric) needed to neutralize all or part of a material's basicity, expressed as milligrams of KOH per gram of sample and can be measured according to ASTM D2896. Optionally, an acidic material, such as carbon dioxide, acetates or boric acid, but typically carbon dioxide, may be added to the reaction mixture.

Overbased compositions or salts are single phase, homogeneous, Newtonian systems characterized by a metal content in excess of that which would be present according to the stoichiometry of the metal and the particular acidic organic compound reacted with the metal. The amount of excess metal is commonly expressed in terms of metal ratio. The term "metal ratio" is the ratio of the total equivalents of the metal to the equivalents of the acidic organic compound, i.e. ([mole equivalents of metal cationic portion plus mole equivalents of metal in the overbased portion] divided by mole equivalents of acidic organic portion). A salt having 4.5 times as much metal as present in a normal salt will have metal excess of 3.5 equivalents, or a ratio of 4.5. These salts typically have a metal ratio of in excess of 0 and generally up to about 40 or more. The term "metal ratio is also explained in standard textbook entitled "Chemistry and Technology of Lubricants", Third Edition, Edited by R. M. Mortier and S. T. Orszulik, Copyright 2010. In one embodiment, the metal ratio is from an excess of 1 up to about 40, preferably from about 1.5 up to about 35, or from about 2 up to about 30, more preferably from about 3 to about 26. In one embodiment the metal ratio is from about 1.5 to about 40, more preferably about 6 to about 35, more preferably about 10 to about 30, more preferably about 15 to about 30. In one embodiment, the metal ratio is from about 12 to 25 or from about 20 to about 30.

The inventors have found that overbasing the hydrocarbyl substituted amine/itaconate reaction product not only improves the friction modifying performance of the compound and its solubility in non-polar media such as a lubricating fluid formulation but also imparts multi-functionality to the compound. That is, the overbased reaction product of a hydrocarbyl substituted amine with an itaconate can function not only as a friction modifier, but, for example, also as a detergent, anti-wear or extreme pressure agent, anti-oxidant and dispersant. Thus, the overbased compound can be used to replace one or more friction modifiers, detergents, anti-wear or extreme pressure agents, anti-oxidants and dispersants or mixtures thereof in a functional fluid formulation. As an anti-wear agent, the TBN of the overbased compounds can play a role in improving the anti-wear performance. As TBN is increase, more free metal becomes available to interact with a surface, preventing wear. The compounds of the invention can also provide a detergent mode of action for improving cleanliness, reducing deposits, and for acid control in addition to friction modification. Because multiple modes of action are incorporated into one compound, the compounds can eliminate competition for the surface of the friction material known to occur between traditional friction modifiers and detergents. In addition, it has been observed that the overbased reaction products described herein can provide improved performance irrespective of temperature, pressure and friction material.

Not only do the overbased reaction products of the present invention exhibit multiple functionalities, the compound can be incorporated into oil of lubricating viscosity at treat rates in excess of the solubility of the non-overbased precursor compounds. For example, traditional non-overbased friction modifiers can generally be included on an active basis (i.e., on an oil free basis) in lubricant formulations up to a treat of about 10 wt %, at which point the compounds begin to drop out of formulation. Often the treat rate of non-overbased friction modifiers is even lower. In contrast, the hydrocarbyl substituted amine/itaconate reaction product can typically be soluble in lubricant formulations up to at least about 40 wt % and sometimes even 50 wt % on an active basis. With respect to engine oil functional fluids, the reaction products described herein may be present between 0.1 wt % to 50 wt % or 0.05 wt % to 40 wt %, or 0.1 to 30 wt %, or 1 to 20 wt % on an active basis. With respect to driveline functional fluids, such as transmission fluids, the reaction products described herein may be present between 0.01 wt % to 15 wt %, or 0.01 wt % to about 10 wt %, or 0.05 wt % to 6 wt %, or 0.1 wt % to 4 wt % or 0.25 wt % to 2.5 wt %, or 0.5 wt % to 1.0 wt % of the fluid composition, on an active basis.

In another embodiment, the invention provides a lubricant composition comprising a major amount of an oil of lubricating viscosity and an overbased salt of an N-substituted 4-carboxypyrrolidin-2-one. Suitable oils include natural and synthetic lubricating oils and mixtures thereof. In a fully formulated lubricant, the oil of lubricating viscosity is generally present in a major amount (i.e. an amount greater than 50 percent by weight). Typically, the oil of lubricating viscosity is present in an amount of 75 to 95 percent by weight, and often greater than 80 percent by weight of the composition. For concentrates, the oil of lubricating viscosity may be present at lower concentration or in a minor amount, for example, from 10 to 50% by weight, and in one embodiment 10 to 30% by weight.

Natural oils useful in making the inventive lubricants and functional fluids include animal oils and vegetable oils as well as mineral lubricating oils such as liquid petroleum oils and solvent-treated or acid-treated mineral lubricating oils of the paraffinic, naphthenic or mixed paraffinic/-naphthenic types which may be further refined by hydrocracking and hydrofinishing processes.

Synthetic lubricating oils include hydrocarbon oils and halo-substituted hydrocarbon oils such as polymerized and interpolymerized olefins, also known as polyalphaolefins; polyphenyls; alkylated diphenyl ethers; alkyl- or dialkylbenzenes; and alkylated diphenyl sulfides; and the derivatives, analogs and homologues thereof. Also included are alkylene oxide polymers and interpolymers and derivatives thereof, in which the terminal hydroxyl groups may have been modified by esterification or etherification. Also included are esters of dicarboxylic acids with a variety of alcohols, or esters made from C5 to C12 monocarboxylic acids and polyols or polyol ethers. Other synthetic oils include silicon-based oils, liquid esters of phosphorus-containing acids, and polymeric tetrahydrofurans. The synthetic oils may be produced by Fischer-Tropsch reactions and typically may comprise hydroisomerized Fischer-Tropsch hydrocarbons and/or waxes, or hydroisomerized slack waxes.

Unrefined, refined and rerefined oils, either natural or synthetic, can be used in the lubricants of the present invention. Unrefined oils are those obtained directly from a natural or synthetic source without further purification treatment. Refined oils have been further treated in one or more purification steps to improve one or more properties. They can, for example, be hydrogenated, resulting in oils of improved stability against oxidation.

In one embodiment, the oil of lubricating viscosity is an API Group II, Group III, Group IV, or Group V oil, including a synthetic oil, or mixtures thereof. These are classifications established by the API Base Oil Interchangeability Guidelines. Both Group II and Group III oils contain ≤0.03 percent sulfur and ≥90 percent saturates. Group II oils have a viscosity index of 80 to 120, and Group III oils have a viscosity index ≥120. Polyalphaolefins are categorized as Group IV. Group V is encompasses "all others" (except for Group I, which contains ≥0.03% S and/or ≤90% saturates and has a viscosity index of 80 to 120).

In one embodiment, at least 50% by weight of the oil of lubricating viscosity is a polyalphaolefin (PAO). Typically, the polyalphaolefins are derived from monomers having from 4 to 30, or from 4 to 20, or from 6 to 16 carbon atoms. Examples of useful PAOs include those derived from 1-decene. These PAOs may have a viscosity of 1.5 to 150 mm$^2$/s (cSt) at 100° C. PAOs are typically hydrogenated materials.

The oils of the present invention can encompass oils of a single viscosity range or a mixture of high viscosity and low viscosity range oils. In one embodiment, the oil exhibits a 100° C. kinematic viscosity of 1 or 2 to 8 or 10 mm$^2$/sec (cSt). The overall lubricant composition may be formulated using oil and other components such that the viscosity at 100° C. is 1 or 1.5 to 10 or 15 or 20 mm$^2$/sec and the Brookfield viscosity (ASTM-D-2983) at −40° C. is less than 20 or 15 Pa-s (20,000 cP or 15,000 cP), such as less than 10 Pa-s, even 5 or less.

Other Performance Additives

A lubricating composition may be prepared by adding to the product described herein optionally other performance additives (as described herein below). The other performance additives include at least one of metal deactivators, viscosity modifiers, detergents, antiwear agents, corrosion inhibitors, dispersants, dispersant viscosity modifiers, extreme pressure agents, antioxidants, foam inhibitors, demulsifiers, pour point depressants, seal swelling agents and mixtures thereof. Typically, fully-formulated lubricating oil will contain one or more of these performance additives.

With regard to driveline devices, antioxidants (that is, oxidation inhibitors), can include hindered phenolic antioxidants, secondary aromatic amine antioxidants such as dinonyldiphenylamine as well as such well-known variants as monononyldiphenylamine and diphenylamines with other alkyl substituents such as mono- or di-ocyl, sulfurized phenolic antioxidants, oil-soluble copper compounds, phosphorus-containing antioxidants, and organic sulfides, disulfides, and polysulfides such as 2-hydroxyalkyl, alkyl thioethers or 1-t-dodecylthio-2-propanol or sulfurized 4-carbobutoxycyclohexene or other sulfurized olefins, or mixtures thereof. In one embodiment the lubricating composition for a driveline device includes an antioxidant, or mixtures thereof. The antioxidant may be present at 0 wt % to 15 wt %, or 0.1 wt % to 10 wt %, or 0.5 wt % to 5 wt %, or 0.5 wt % to 3 wt %, or 0.3 wt % to 1.5 wt % of the lubricating composition.

The hindered phenol antioxidant often contains a secondary butyl and/or a tertiary butyl group as a sterically hindering group. The phenol group may be further substituted with a hydrocarbyl group (typically linear or branched alkyl) and/or a bridging group linking to a secondary aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester and may include, e.g., Irganox™ L-135 from Ciba. A more detailed description of suitable ester-containing hindered phenol antioxidant chemistry is found in U.S. Pat. No. 6,559,105.

With regard to engine oil lubricating compositions, antioxidants can include those described above and additionally diarylamines, alkylated diarylamines, molybdenum compounds (such as molybdenum dithiocarbamates), hydroxyl thioethers, and mixtures thereof, for example. The diarylamine or alkylated diarylamine may be phenyl-α-naphthylamine (PANA), an alkylated diphenylamine, or an alkylated phenylnapthylamine, or mixtures thereof. The alkylated diphenylamine may include di-nonylated diphenylamine, nonyl diphenylamine, octyl diphenylamine, di-octylated diphenylamine, di-decylated diphenylamine, decyl diphenylamine and mixtures thereof. In one embodiment the diphenylamine may include nonyl diphenylamine, dinonyl diphenylamine, octyl diphenylamine, dioctyl diphenylamine, or mixtures thereof. In one embodiment the diphenylamine may include nonyl diphenylamine, or dinonyl diphenylamine. The alkylated diarylamine may include octyl, di-octyl, nonyl, di-nonyl, decyl or di-decyl phenylnapthylamines.

Examples of molybdenum dithiocarbamates which may be used as an antioxidant include commercial materials sold under the trade names such as Vanlube 822™ and Molyvan™ A from R. T. Vanderbilt Co., Ltd., and Adeka Sakura-Lube™ S-100, S-165, S-600 and 525, or mixtures thereof.

In one embodiment for driveline applications, the lubricating composition further includes a viscosity modifier (VM) or dispersant viscosity modifier (DVM). The VM is known in the art and may include, ethylene-propylene copolymers, polymethacrylates, polyacrylates, polyalkyl styrenes, polyolefins, esters of maleic anhydride-olefin copolymers (such as those described in International Application WO 2010/014655), esters of maleic anhydride-styrene copolymers, or mixtures thereof.

The DVM may include functionalized polyolefins, for example, ethylene-propylene copolymers that have been functionalized with an acylating agent such as maleic anhydride and an amine; polymethacrylates functionalized with an amine, or styrene-maleic anhydride copolymers reacted with an amine. More detailed description of dispersant viscosity modifiers are disclosed in International Publication WO2006/015130 or U.S. Pat. Nos. 4,863,623; 6,107,257; 6,107,258; and 6,117,825. In one embodiment the dispersant viscosity modifier may include those described in U.S. Pat. No. 4,863,623 (see column 2, line 15 to column 3, line 52) or in International Publication WO2006/015130 (see page 2, paragraph [0008] and preparative examples are described paragraphs [0065] to [0073]).

With regard to engine oil lubricating compositions, VMs or DVMs can include those described above and additionally hydrogenated styrene-isoprene polymers, hydrogenated diene polymers, hydrogenated styrene-butadiene rubbers.

Examples of commercially available VMs, DVMs and their chemical types may include the following: polyisobutylenes (such as Indopol™ from BP Amoco or Parapol™ from ExxonMobil); olefin copolymers (such as Lubrizol™ 7060, 7065, and 7067 from Lubrizol and Lucant™ HC-2000L and HC-600 from Mitsui); hydrogenated styrene-diene copolymers (such as Shellvis™ 40 and 50, from Shell and LZ® 7308, and 7318 from Lubrizol); styrene/maleate copolymers, which are dispersant copolymers (such as LZ® 3702 and 3715 from Lubrizol); polymethacrylates, some of which have dispersant properties (such as those in the Viscoplex™ series from RohMax, the Hitec™ series from Afton, and LZ 7702™, LZ 7727™, LZ 7725™ and LZ 7720C™ from Lubrizol); olefin-graft-polymethacrylate polymers (such as Viscoplex™ 2-500 and 2-600 from RohMax); and hydrogenated polyisoprene star polymers (such as Shellvis™ 200 and 260, from Shell). Also included are Asteric™ polymers from Lubrizol (methacrylate polymers with radial or star architecture). Viscosity modifiers that may be used are described in U.S. Pat. Nos. 5,157,088, 5,256,752 and 5,395,539.

In one embodiment the lubricating composition of the invention further comprises a VM. In another embodiment, the lubricating composition further comprises a DVM. The VM or DVM may be present at 0 wt % to 15 wt %, or 0 wt % to 10 wt %, or 0.05 wt % to 5 wt %, or 0.2 wt % to 2 wt % of the lubricating composition.

In another embodiment the lubricating composition may comprise one or more DVM from 0 to 40 wt %.

The lubricating composition may further include a dispersant, or mixtures thereof. The further dispersant may be described as "other than an amine compound as described above" in the event that some of the amine compounds described above may exhibit some dispersant characteristics. Examples of "carboxylic dispersants" are described in many U.S. Pat. Nos. including the following: U.S. Pat. Nos. 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, Re 26,433, and U.S. Pat. No. 6,165,235.

The dispersant may be a succinimide dispersant, a Mannich dispersant, a succinamide dispersant, a polyolefin succinic acid ester, amide, or ester-amide, or mixtures thereof. In one embodiment the dispersant may be present as a single dispersant. In one embodiment the dispersant may be present as a mixture of two or three different dispersants, wherein at least one may be a succinimide dispersant.

The succinimide dispersant may be derived from an aliphatic polyamine, or mixtures thereof. The aliphatic polyamine may be aliphatic polyamine such as an ethylenepolyamine, a propylenepolyamine, a butylenepolyamine, or mixtures thereof. In one embodiment the aliphatic polyamine may be ethylenepolyamine. In one embodiment the aliphatic polyamine may be selected from the group consisting of ethylenediamine, diethylenetriamine, triethylenetetramine, tetraethylenepentamine, pentaethylenehexamine, polyamine still bottoms, and mixtures thereof.

The succinimide dispersant may be derived from an aromatic amine, aromatic polyamine, or mixtures thereof. The aromatic amine may have one or more aromatic moieties linked by a hydrocarbylene group and/or a heteroatom. In certain embodiments, the aromatic amine may be a nitro-substituted aromatic amine. Examples of nitro-substituted aromatic amines include 2-nitroaniline, 3-nitroaniline, and 4-nitroaniline (typically 3-nitroaniline). Other aromatic amines may be present along with the nitroaniline described herein. Condensation products with nitroaniline and optionally also with Disperse Orange 3 (that is, 4-(4-nitrophenylazo)aniline) are known from US Patent Application 2006/0025316.

The succinimide dispersant may be derived from 4-aminodiphenylamine (ADPA), methylene coupled ADPA, or mixtures thereof succinimide dispersant derived from 4-aminodiphenylamine include those disclosed in International Patent Applications WO2010/062842 or WO2010/099136.

In one embodiment the dispersant may be a polyolefin succinic acid ester, amide, or ester-amide. For instance, a polyolefin succinic acid ester may be a polyisobutylene succinic acid ester of pentaerythritol, or mixtures thereof. A polyolefin succinic acid ester-amide may be a polyisobutylene succinic acid reacted with an alcohol (such as pentaerythritol) and an amine.

The dispersant may be an N-substituted long chain alkenyl succinimide. An example of an N-substituted long chain alkenyl succinimide is polyisobutylene succinimide. Typically the polyisobutylene from which polyisobutylene succinic anhydride is derived has a number average molecular weight of 350 to 5000, or 550 to 3000 or 750 to 2500. Succinimide dispersants and their preparation are disclosed, for instance in U.S. Pat. Nos. 3,172,892, 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, Re 26,433, and U.S. Pat. Nos. 6,165,235, 7,238,650 and EP Patent Application 0 355 895 A.

"Amine dispersants" are reaction products of relatively high molecular weight aliphatic or alicyclic halides and amines, such as polyalkylene polyamines. Examples thereof are described in the following U.S. Pat. Nos. 3,275,554, 3,438,757, 3,454,555, and 3,565,804.

"Mannich dispersants" are the reaction products of alkyl phenols in which the alkyl group contains at least 30 carbon atoms with aldehydes (especially formaldehyde) and amines (especially polyalkylene polyamines). The materials described in the following U.S. Pat. Nos. are illustrative: U.S. Pat. Nos. 3,036,003, 3,236,770, 3,414,347, 3,448,047, 3,461,172, 3,539,633, 3,586,629, 3,591,598, 3,634,515, 3,725,480, 3,726,882, and 3,980,569.

The dispersants may also be post-treated by conventional methods by a reaction with any of a variety of agents. Among these are boron compounds (such as boric acid), urea, thiourea, dimercaptothiadiazoles, carbon disulfide, aldehydes, ketones, carboxylic acids such as terephthalic acid, hydrocarbon-substituted succinic anhydrides, maleic anhydride, nitriles, epoxides, and phosphorus compounds such as phosphorus acids or anhydrides. In one embodiment the post-treated dispersant is borated. In one embodiment the post-treated dispersant may be a dispersant reacted with dimercaptothiadiazoles. In one embodiment the post-treated dispersant may be a dispersant reacted with phosphoric or phosphorous acid. Exemplary materials of this kind are described in the following U.S. Pat. Nos. 3,200,107, 3,282,955, 3,367,943, 3,513,093, 3,639,242, 3,649,659, 3,442,808, 3,455,832, 3,579,450, 3,600,372, 3,702,757, and 3,708,422.

The dispersant may be present at 0.01 wt % to 20 wt %, or 0.1 wt % to 15 wt %, or 0.1 wt % to 10 wt %, or 1 wt % to 6 wt %, or 1 to 4 wt % of the lubricating composition.

Mixtures of dispersants can also be used. The amount of dispersant or dispersants, if present in formulations of the present technology, is generally 0.3 to 10 percent by weight. In other embodiments, the amount of dispersant is 0.5 to 7 percent or 1 to 5 percent of the final blended fluid formulation. In a concentrate, the amounts will be proportionately higher.

In one embodiment the invention provides a lubricating composition further comprising an overbased metal-containing detergent in addition to the overbased friction modifier described above, which in some embodiments might also be considered to be a detergent. The metal of the metal-containing detergent may be zinc, sodium, calcium, barium, or magnesium. Typically the metal of the metal-containing detergent may be sodium, calcium, or magnesium.

The overbased metal-containing detergent may be selected from the group consisting of non-sulfur containing phenates, sulfur containing phenates, sulfonates, carboxylates, salixarates, salicylates, and mixtures thereof, or borated equivalents thereof. The metal portion of the detergent is an alkali or alkaline earth metal. Suitable metals include sodium, calcium, potassium and magnesium. Typically, the detergents are overbased, meaning that there is a stoichiometric excess of metal base over that needed to form the neutral metal salt. The overbased detergent may be borated with a borating agent such as boric acid.

The overbased metal-containing detergent may also include "hybrid" detergents formed with mixed surfactant systems including phenate and/or sulfonate components, for example, phenate/salicylates, sulfonate/phenates, sulfonate/salicylates, sulfonates/phenates/salicylates, as described; for example, in U.S. Pat. Nos. 6,429,178; 6,429,179; 6,153,565; and 6,281,179. Where, for example, a hybrid sulfonate/phenate detergent may be employed, the hybrid detergent would be considered equivalent to amounts of distinct phenate and sulfonate detergents introducing like amounts of phenate and sulfonate soaps, respectively.

Typically an overbased metal-containing detergent may be a zinc, sodium, calcium, potassium, or magnesium salt of a phenate, sulfur containing phenate, sulfonate, salixarate or salicylate. Overbased salixarates, phenates and salicylates typically have a total base number of 180 to 450 TBN. Overbased sulfonates typically have a total base number of 250 to 600, or 300 to 500. Overbased detergents are known in the art. In one embodiment the sulfonate detergent may be predominantly a linear alkylbenzene sulfonate detergent having a metal ratio of at least 8 as is described in paragraphs [0026] to [0037] of US Patent Application 2005065045 (and granted as U.S. Pat. No. 7,407,919). The linear alkylbenzene sulfonate detergent may be particularly useful for assisting in improving fuel economy. Linear alkylbenzene sulfonates are often derived from linear alpha-olefins through an alkylation of benzene or toluene to give the linear alkylbenzene which is subsequently sulfonated. The aromatic ring may by attached anywhere on the chain, typically at the 2, 3 or 4 position. The isomers of the linear alkylbenzenes occur through positional isomerization during the alkylation reaction or through positional isomerization of the double bond of the olefin prior to alkylation. Often the linear alkylbenzenes are mixtures resulting in sulfonate detergents with good solubility as well as their ability to impart improved fuel economy.

Typically the overbased metal-containing detergent may be a calcium or magnesium overbased detergent.

The compositions of the present invention can also include at least one phosphorus acid, phosphorus acid salt, phosphorus acid ester or derivative thereof including sulfur-containing analogs in the amount of 0.002-1.0 weight percent. The phosphorus acids, salts, esters or derivatives thereof include phosphoric acid, phosphorous acid, phosphorus acid esters or salts thereof, phosphites, phosphorus-containing amides, phosphorus-containing carboxylic acids or esters, phosphorus-containing ethers, and mixtures thereof.

In one embodiment, the phosphorus acid, ester or derivative can be an organic or inorganic phosphorus acid, phosphorus acid ester, phosphorus acid salt, or derivative thereof. The phosphorus acids include the phosphoric, phosphonic, phosphinic, and thiophosphoric acids including dithiophosphoric acid as well as the monothiophosphoric, thiophosphinic and thiophosphonic acids. One group of phosphorus compounds are alkylphosphoric acid mono alkyl primary amine salts as represented by the formula

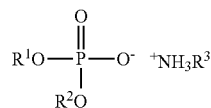

where $R^1$, $R^2$, $R^3$ are alkyl or hydrocarbyl groups or one of $R^1$ and $R^2$ can be H. The materials can be a 1:1 mixture of dialkyl and monoalkyl phosphoric acid esters. Compounds of this type are described in U.S. Pat. No. 5,354,484.

Eighty-five percent phosphoric acid is a suitable material for addition to the fully-formulated compositions and can be included at a level of 0.01-0.3 weight percent based on the weight of the composition, such as 0.03 to 0.2 or to 0.1 percent.

Other phosphorus-containing materials that may be present include dialkylphosphites (sometimes referred to as dialkyl hydrogen phosphonates) such as dibutyl phosphite. Yet other phosphorus materials include phosphorylated hydroxy-substituted triesters of phosphorothioic acids and amine salts thereof, as well as sulfur-free hydroxy-substituted di-esters of phosphoric acid, sulphur-free phosphorylated hydroxy-substituted di- or tri-esters of phosphoric acid, and amine salts thereof. These materials are further described in U.S. patent application US 2008-0182770.

Extreme Pressure (EP) agents that are soluble in the oil include sulfur- and chlorosulfur-containing EP agents, dimercaptothiadiazole or $CS_2$ derivatives of dispersants (typically succinimide dispersants), derivative of chlorinated hydrocarbon EP agents and phosphorus EP agents. Examples of such EP agents include chlorinated wax; sulfurized olefins (such as sulfurized isobutylene), a hydrocarbyl-substituted 2,5-dimercapto-1,3,4-thiadiazole, or oligomers thereof, organic sulfides and polysulfides such as dibenzyldisulfide, bis-(chlorobenzyl) disulfide, dibutyl tetrasulfide, sulfurized methyl ester of oleic acid, sulfurized alkylphenol, sulfurized dipentene, sulfurized terpene, and sulfurized Diels-Alder adducts; phosphosulfurized hydrocarbons such as the reaction product of phosphorus sulphide with turpentine or methyl oleate; phosphorus esters such as the dihydrocarbon and trihydrocarbon phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenol phosphite; metal thiocarbamates such as zinc dioctyldithiocarbamate and barium heptylphenol diacid; amine salts of alkyl and dialkylphosphoric acids or derivatives including, for example, the amine salt of a reaction product of a dialkyl-dithiophosphoric acid with propylene oxide and subsequently followed by a further reaction with $P_2O_5$; and mixtures thereof (as described in U.S. Pat. No. 3,197,405).

Foam inhibitors that may be useful in the compositions of the invention include polysiloxanes, copolymers of ethyl acrylate and 2-ethylhexyl acrylate and optionally vinyl acetate; demulsifiers including fluorinated polysiloxanes, trialkyl phosphates, and various polymers and copolymers of ethylene glycol, such as polyethylene glycols, polymers and copolymers of ethylene oxide, such as polyethylene oxides, and polymers and copolymers of propylene oxide, such as polypropylene oxides and (ethylene oxide-propylene oxide) polymers, or mixtures thereof.

Pour point depressants that may be useful in the compositions of the invention include alkylnaphthalenes, vinyl acetate/fumarate or /maleate copolymers, styrene/maleate copolymers, polyalphaolefins, esters of maleic anhydride-styrene copolymers, poly(meth)acrylates, polyacrylates or polyacrylamides.

Metal deactivators include derivatives of benzotriazoles (typically tolyltriazole), 1,2,4-triazoles, benzimidazoles, 2-alkyldithiobenzimidazoles or 2-alkyldithiobenzothiazoles, and dimercaptothiadiazole. The metal deactivators may also be described as corrosion inhibitors.

Other optional components include seal swell compositions, such as isodecyl sulfolane or phthalate esters, which are designed to keep seals pliable. Seal swell agents include sulfolene derivatives Exxon Necton37™ (FN 1380) and Exxon Mineral Seal Oil™ (FN 3200), as well as Power-Zol™ from Lubrizol.

The lubricating composition optionally may further include at least one antiwear agent. Examples of suitable antiwear agents include titanium compounds, tartrates, tartrimides, oil soluble amine salts of phosphorus compounds, sulfurized olefins, metal dihydrocarbyldithiophosphates (such as zinc dialkyldithiophosphates), phosphites (such as dibutyl phosphite), phosphonates, thiocarbamate-containing compounds, such as thiocarbamate esters, thiocarbamate amides, thiocarbamic ethers, alkylene-coupled thiocarbamates, and bis(S-alkyldithiocarbamyl) disulphides. The antiwear agent may in one embodiment include a tartrate, or tartrimide as disclosed in International Publication WO 2006/044411 or Canadian Patent CA 1 183 125. The tartrate or tartrimide may contain alkyl-ester groups, where the sum of carbon atoms on the alkyl groups may be at least 8. The antiwear agent may in one embodiment include a citrate as is disclosed in US Patent Application 20050198894.

Another class of additives includes oil-soluble titanium compounds as disclosed in U.S. Pat. No. 7,727,943 and US2006/0014651. The oil-soluble titanium compounds may function as antiwear agents, friction modifiers, antioxidants, deposit control additives, or more than one of these functions. In one embodiment the oil soluble titanium compound is a titanium (IV) alkoxide. The titanium alkoxide is formed from a monohydric alcohol, a polyol or mixtures thereof. The monohydric alkoxides may have 2 to 16, or 3 to 10 carbon atoms. In one embodiment, the titanium alkoxide is titanium (IV) isopropoxide. In one embodiment, the titanium alkoxide is titanium (IV) 2-ethylhexoxide. In one embodiment, the titanium compound comprises the alkoxide of a vicinal 1,2-diol or polyol. In one embodiment, the 1,2-vicinal diol comprises a fatty acid mono-ester of glycerol, often the fatty acid is oleic acid.

In one embodiment, the oil soluble titanium compound is a titanium carboxylate. In one embodiment the titanium (IV) carboxylate is titanium neodecanoate.

In one embodiment the oil soluble titanium compound may be present in the lubricating composition in an amount necessary to provide for 10 ppm to 1500 ppm titanium by weight or 25 ppm to 150 ppm titanium by weight.

If the lubricating composition is part of a grease composition, the composition further comprises a thickener. The thickener may include simple metal soap thickeners, soap complexes, non-soap thickeners, metal salts of such acid-functionalized oils, polyurea and diurea thickeners, calcium sulfonate thickeners or mixtures thereof. Thickeners for grease are well known in the art.

A driveline device lubricating composition in different embodiments may have a composition as disclosed in the following table, where A can be an auto gear oil, B can be an automatic transmission fluid, and C can be an off-highway vehicle oil:

| Additive | Embodiments (wt %) | | |
|---|---|---|---|
| | A | B | C |
| Compounds of Invention | 0.25 to 2.5 | 0.1 to 5 | 0.01 to 10 |
| Dispersant | 1 to 4 | 2 to 7 | 0 to 5 |
| Extreme Pressure Agent | 3 to 6 | 0 to 6 | 0 to 3 |
| Overbased Detergent | 0 to 1 | 0.01 to 2 | 0.5 to 6 |
| Antioxidant | 0 to 5 | 0.01 to 2 | 0 to 3 |
| Antiwear Agent | 0.5 to 5 | 0.01 to 3 | 0.5 to 3 |
| Viscosity Modifier | 0.1 to 70 | 0.1 to 15 | 1 to 60 |
| Any Other Performance Additive | 0 to 10 | 0 to 8 | 0 to 6 |
| Oil of Lubricating Viscosity | Balance to 100% | Balance to 100% | Balance to 100% |

An engine lubricating composition in different embodiments may have a composition as disclosed in the following table:

| Additive | Embodiments (wt %) | | |
|---|---|---|---|
| | A | B | C |
| Compounds of Invention | 0.25 to 2.5 | 0.1 to 5 | 0.01 to 10 |
| Dispersant | 0 to 12 | 0 to 8 | 0.5 to 6 |
| Dispersant Viscosity Modifier | 0 to 5 | 0 to 4 | 0.05 to 2 |
| Overbased Detergent | 0.1 to 15 | 0.1 to 10 | 0.2 to 8 |
| Antioxidant | 0.1 to 13 | 0.1 to 10 | 0.5 to 5 |
| Antiwear Agent | 0.1 to 15 | 0.1 to 10 | 0.3 to 5 |
| Viscosity Modifier | 0 to 10 | 0.5 to 8 | 1 to 6 |
| Any Other Performance Additive | 0 to 10 | 0 to 8 | 0 to 6 |
| Oil of Lubricating Viscosity | Balance to 100% | Balance to 100% | Balance to 100% |

The above components can be in the form of a fully-formulated lubricant or in the form of a concentrate within a smaller amount of lubricating oil. If they are present in a concentrate, their concentrations will generally be directly proportional to their concentrations in the more dilute form in the final blend.

INDUSTRIAL APPLICATION

The lubricating composition of the present invention may be a useful additive in a driveline device, an internal combustion engine, a hydraulic system, a grease, a turbine, or a refrigerant or any other functional fluid.

It has been found that the compounds disclosed herein can provide at least one of wet clutch friction modification, antiwear, detergent, anti-oxidant, and dispersant performance in driveline devices. For example, in one embodiment the compounds disclosed herein can be employed in an ATF lubricant composition to provide friction modification. In another example embodiment, the compounds disclosed herein can be employed in MTF formulations to provide antiwear functionality while maintaining correct friction for smooth gear change.

An automatic transmission includes continuously variable transmissions (CVT), infinitely variable transmissions (IVT), toroidal transmissions, continuously slipping torque converter clutches (CSTCC), stepped automatic transmissions or dual clutch transmissions (DCT). Automatic transmissions can contain continuously slipping torque converter clutches (CSTCC), wet start and shifting clutches and in some cases may also include metal or composite synchronizers. Dual clutch transmissions or automatic transmissions may also incorporate electric motor units to provide a hybrid drive.

An MTF lubricant composition containing the overbased compounds described above may be used in a manual gearbox which may be unsynchronized or may contain a synchronizer mechanism. The gearbox may be self-contained or may additionally contain any of a transfer gearbox, planetary gear system, differential, limited slip differential or torque vectoring device, which may be lubricated by a manual transmission fluid.

For MTF lubricating compositions, the overbased compounds can help deliver metal to the synchronizer surface, thereby helping to minimize synchronizer wear, while also maintaining the correct friction for a smooth gear change (i.e. low static friction combined with stable dynamic). Further, because the overbased compounds can function as a detergent, the compounds can give synchronizer wear protection in the absence of detergent, i.e. a tribofilm can form offering protection when the overbased compounds are used. The frictional appetite of a synchronizer will differ dependant on the synchronizer composition. For example, some materials may operate better with a high TBN, or some may operate better with a linear or branched underlying non-overbased compound, and the overbased compounds described above can be modified to suit the particular purpose.

Automatic transmission fluids must have a good friction versus sliding speed relationship, or an objectionable phenomenon called shudder will occur in the vehicle. Transmission shudder is a self-excited vibrational state also called "stick-slip" or "dynamic frictional vibration," generally occurring in slipping torque converter clutches. The friction characteristics of the fluid and material system, combined with the mechanical design and controls of the transmission, determine the susceptibility of the transmission to shudder. The overbased compounds described herein can provide excellent anti-shudder durability.

A plot of the measured coefficient of friction ($\mu$) versus sliding speed (V), commonly called a $\mu$-V curve, has been shown to correlate to transmission shudder. Both theory and experiments support the region of positive to slightly negative slope of this $\mu$-V curve to correlate to good anti-shudder performance of transmission fluids. A fluid which allows the vehicle to operate without vibration or shudder is said to have good anti-shudder performance. The fluid should maintain those characteristics over its service lifetime. The longevity of the anti-shudder performance in the vehicle is commonly referred to as "anti-shudder durability".

The variable speed friction tester (VSFT) measures the coefficient of friction with respect to sliding speed simulating the speeds, loads, and friction materials found in transmission clutches and correlates to the performance found in actual use. The procedures are well documented in the literature; see for example Society of Automotive Engineers publication #941883.

The screen test for anti-shudder durability can be the VSFT-JASO Anti-shudder test. The VSFT apparatus consists of a disc that can be metal or another friction material which is rotated against a metal surface. The friction materials employed in the particular tests are various commercial friction materials commonly used in automatic transmission clutches, as indicated in the Tables. The test is run over three temperatures and two load levels. The coefficient of friction measured by the VSFT is plotted against the sliding speed (50 and 200 r.p.m.) over a number speed sweeps at a constant pressure. The results are sometimes presented as slope of the μ-V curve as a function of time, reported for 40, 80, and 120° C. and 24 kg and 40 kg (235 and 392 N) force, determined at 4 hour intervals from 0 to 52 hours. Typically, the slope will initially be positive, with a certain amount of variability, and may gradually decrease, possibly becoming negative after a certain period of time. Longer duration of positive slope is desired.

The data is initially collected as a table of slope values as a function of time, for each run. For ease of analysis and comparison, each formulation at each temperature is assigned a "slope score." At each temperature, the fraction of slope values within the first 7 time measurements (0 to 24 hours) at 24 kg and of the first 7 measurements at 40 kg (thus 14 measurements total) that are positive, as a percent, is denoted as "A". The fraction of the slope values at the two pressures (14 measurements total) within the second 24 hours (28-52 hours) that are positive are denoted as "B". The slope score is defined as A+2B. The extra weighting given to the latter portion of the test is to reflect the greater importance (and difficulty) of preparing a durable fluid that retains a positive slope in the latter stages of the test. The maximum score of 300 denotes a fluid that exhibits a consistently positive slope through the entire test. A more detailed description of the slope score reporting summary and an illustrative calculation of a slope score is found in U.S. Patent Publication 2010-0210490, Vickerman et al., published Aug. 19, 2010; see paragraphs 0093 to 0096.

Example Slope Score Calculation

|   | Time (hr) | μ-V slope 24 kg | μ-V slope 40 kg | Section Result | Slope Score (A + 2B) |
|---|---|---|---|---|---|
| A Temp ° C. | 0 | −0.009 | −0.010 | only 1 positive result (0.003) out of 14 = 1/14 = 7.14% | 7.14 + (2 · 7.14) = 21.42 |
|   | 4 | −0.012 | −0.003 |   |   |
|   | 8 | −0.019 | −0.009 |   |   |
|   | 12 | −0.021 | −0.004 |   |   |
|   | 16 | −0.020 | −0.004 |   |   |
|   | 20 | −0.021 | 0.003 |   |   |
|   | 24 | −0 016 | −0.010 |   |   |
| B Temp ° C. | 28 | −0 015 | −0.002 | only 1 positive result (0.001) out of 14 1/14 = 7.14% |   |
|   | 32 | −0.014 | −0.00 |   |   |
|   | 36 | −0.012 | 0.001 |   |   |
|   | 40 | −0.011 | −0.008 |   |   |
|   | 44 | −0.012 | −0.006 |   |   |
|   | 48 | −0.013 | −0.013 |   |   |
|   | 52 | −0.017 | −0.009 |   |   |

The compounds disclosed herein have shown slope scores of between 50 and 300 at 40° C., 100 and 300 at 80° C., and between 200 and 300 at 120° C. in ATF lubricant compositions.

The compounds disclosed can be tested for synchronizer friction and wear in manual transmission fluids as well. Generally, the test involves an initial break-in phase in which the composition is subjected to a number of cycles of the transmission, typically 100 cycles. A performance phase is then completed in which a number of frictional measurements are taken at defined speeds. A durability phase follows whereby dynamic friction is measured at a number of defined cycles from 0 to 10,000. After the durability performance phase, a number of frictional measurements are taken at defined speeds, and a final static friction measurement is taken.

A good result encompasses several different variables. Dynamic friction should be stable throughout the test, as well as showing an appropriately high value when compared to static friction. Static friction should again be stable during the whole test as well as showing an appropriately low value when compared against dynamic friction. Lower static friction is advantageous. The ratio of static/dynamic friction should be close to a value of 1. In terms of wear, the weight loss from the testing material should be as low as possible. The compounds of the present invention have shown good results when subjected to synchronizer testing.

In one embodiment the method and lubricating composition of the invention may be suitable for other driveline devices. Other driveline device lubricants may include, for example, gear oils, axle oils, drive shaft oils, traction oils, or off highway oils (such as a farm tractor oil).

In one embodiment the invention provides a method of lubricating an internal combustion engine. The engine components may have a surface of steel or aluminum.

In one embodiment the internal combustion engine may be a diesel fuelled engine (typically a heavy duty diesel engine), a gasoline fuelled engine, a natural gas fuelled engine, a mixed gasoline/alcohol fuelled engine, or a hydrogen fuelled internal combustion engine. In one embodiment the internal combustion engine may be a diesel fuelled engine and in another embodiment a gasoline fuelled engine. In one embodiment the internal combustion engine may be a heavy duty diesel engine.

The internal combustion engine may be a 2-stroke or 4-stroke engine. Suitable internal combustion engines include marine diesel engines, aviation piston engines, low-load diesel engines, and automobile and truck engines. The marine diesel engine may be lubricated with a marine diesel cylinder lubricant (typically in a 2-stroke engine), a system oil (typically in a 2-stroke engine), or a crankcase lubricant (typically in a 4-stroke engine).

The lubricant composition for an internal combustion engine may be suitable for any engine lubricant irrespective of the sulfur, phosphorus or sulfated ash (ASTM D-874) content. The sulfur content of the engine oil lubricant may be 1 wt % or less, or 0.8 wt % or less, or 0.5 wt % or less, or 0.3 wt % or less. In one embodiment the sulfur content may be in the range of 0.001 wt % to 0.5 wt %, or 0.01 wt % to 0.3 wt %. The phosphorus content may be 0.2 wt % or less, or 0.12 wt % or less, or 0.1 wt % or less, or 0.085 wt % or less, or 0.08 wt % or less, or even 0.06 wt % or less, 0.055 wt % or less, or 0.05 wt % or less. In one embodiment the phosphorus content may be 0.04 wt % to 0.12 wt %. In one embodiment the phosphorus content may be 100 ppm to 1000 ppm, or 200 ppm to 600 ppm. In one embodiment the zinc content may be 0.2 wt % or less, or 0.13 wt % or less, or 0.1 wt % or less, or even 0.05% or less. In one embodiment the zinc content may be 0.01 wt % to 0.2 wt %. In one embodiment, the composition may be free of zinc. The total sulfated ash content may be 0.3 wt % to 1.2 wt %, or 0.5 wt % to 1.1 wt % of the lubricating composition. In one embodiment the sulfated ash content may be 0.5 wt % to 1.1 wt % of the lubricating composition.

In one embodiment the lubricating composition may be an engine oil, wherein the lubricating composition may be characterized as having at least one of (i) a sulfur content of 0.5 wt % or less, (ii) a phosphorus content of 0.12 wt % or less, and (iii) a sulphated ash content of 0.5 wt % to 1.1 wt % of the lubricating composition.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements. Multiple groups represented by the same symbol in the formulae described above, may be the same or different.

It is known that some of the materials described above may interact in the final formulation, so that the components of the final formulation may be different from those that are initially added. The products formed thereby, including the products formed upon employing lubricating composition of the present invention in its intended use, may not be susceptible of easy description. Nevertheless, all such modifications and reaction products are included within the scope of the present invention; the present invention encompasses lubricating composition prepared by admixing the components described above.

The following examples provide illustrations of the invention. These examples are non-exhaustive and are not intended to limit the scope of the invention.

EXAMPLES

Example 1

Preparation of Sample 1; an Overbased Salt of the Reaction Product of an N,N-Dialkyl Diamine and Dimethyl Itaconate Part One Duomeen® 2HT (AkzoNobel) and dimethyl itaconate are mixed together in solvent and heated to form a cyclized product. Solvent is removed from the resulting reaction.

Part Two

The cyclized reaction product of Part One is added to solvent and heated. Lime ($Ca(OH)_2$) is added, followed by sparging of carbon dioxide. In total three charges of lime and three separate sparges of carbon dioxide are completed. All solvent is then removed by heating the reaction to 150° C., followed by filtering the product mixture through a filter aid. Where viscous, solvent is added to aid the filtration and later removed by distillation.

The solubility of reaction product of Part Two is tested against the solubility of the non-overbased precursor of Sample 1. It is found that the non-overbased sample can only be treated, on an active basis, between 2 to 15 wt % before it starts dropping out of the oil. In contrast, the overbased formulation of Sample 1 can be solubilized up to 40 wt % without dropping out of the oil.

Example 2

Preparation of Sample 2; an Overbased Salt of the Reaction Product of an Alkyl Tetraamine and Dimethyl Itaconate Tetrameen® T (AkzoNobel) and dimethyl itaconate are reacted according to the same procedure employed in example 1 to produce an overbased product of Sample 2.

Example 3

Screen Test for Anti-Shudder Durability in an Automatic Transmission

The overbased compounds of examples 1-3 are tested for friction modification performance in a standard automatic transmission fluid (ATF) blend shown below. The formulation contains no other detergent or friction modifier components. This represents a more severe fluid than standard ATFs in which to test the performance of the overbased compounds of this invention. The screening is carried out using the VSFT-JASO on Raybestos 4211 and BW6100 friction materials. The VSFT-JASO predicts anti-shudder durability. The ingredients in the formulation below are presented on an active basis, i.e. absent diluent oil. Where the formulation does not add to 100%, it can be assumed diluent oil in conjunction with other typical ATF ingredients, such as dyes, fragrances, anti-foam agents, etc., makes up the difference.

TABLE 1

Slope Scores for Friction Modifier Sample 1; treat rates in ATF formulation tested on Raybestos 4211 friction material

| ATF Formulation | 100% |
|---|---|
| Oil | 84.24 |
| Dispersant | 1.95 |
| Antiwear agent | 0.20 |
| Phosphoric acid | 0.08 |
| Antioxidant | 0.89 |
| Seal Swell Agent | 0.40 |
| Pour Point Depressant | 0.10 |
| Viscosity Modifier | 2.38 |
| Friction Modifier of the present technology | n % |

| | n wt % | | | | |
|---|---|---|---|---|---|
| Temp ° C. | 0.0% | 2.5% | 1.25% | 0.5% | 0.25% |
| 40 | 0 | 300 | 300 | 242.86 | 85.71 |
| 80 | 14.29 | 300 | 300 | 257.14 | 121.44 |
| 120 | 200 | 300 | 300 | 285.72 | 157.14 |

TABLE 2

Slope Scores for Friction Modifier Sample 2; treat rates in ATF formulation tested on BW6100 friction material

| | n wt % | | |
|---|---|---|---|
| Temp ° C. | 0.0% | 0.5% (TBN 200 mg/KOH/g) | 1.0% (TBN 200 mg/KOH/g) | 0.5% (TBN 300 mg/KOH/g) |
| 40 | 0 | 128.57 | 200 | 85.72 |
| 80 | 21.43 | 185.7 | 250 | 200 |
| 120 | 128.57 | 200 | 300 | 200 |

Example 4

Screen Test for Antiwear Durability in a Manual Transmission

A baseline manual transmission formulation containing the additives shown in Table 3 below was used to assess the efficacy of the invention. The baseline formulation does not contain detergents or friction modifiers.

MTF Formulation

| Ingredient | Treat Wt % |
| --- | --- |
| Oil | 100 |
| Thickener | 8 |
| Dispersant | 2.0 |
| Antioxidant | 0.5 |
| extreme pressure agent | 0.2 |
| Antiwear | 0.2 |
| Product of Invention | X |

The formulations were assessed using a synchronizer test apparatus manufactured by Automax®. The test evaluates frictional and lubricating characteristics of synchronizers used in manual transmissions.

The Automax® synchronizer test procedure involves an initial break in phase (100 cycles) followed by an initial performance phase, whereby a number of frictional measurements are taken at defined speeds. A durability phase follows whereby the dynamic friction is measured at a number of defined cycles from 0-10000. After the durability performance phase, a number of frictional measurements are taken at defined speeds and finally a static friction measurement is taken.

For the durability section of the test, stable friction over all 10,000 (10 k) cycles is required, no change in friction from cycle 1 to 10000 is ideal. $\mu_s/\mu_d$ is attempting to describe the shift quality and looks at the difference in friction at 1000 rpm (dynamic) and low speed (static friction). Ideally a value close to 1 is required; this would demonstrate similar frictional properties at high and low speeds.

As can be seen in Table 3, the addition of the overbased friction modifier provides several levels of performance. Inclusion of an overbased friction modifier in Samples 1 and 2 shows benefits over the Reference sample by exhibiting lower static friction and having a $\mu_S/\mu_D$ value closer to 1. Likewise, Samples 1 and 2 show improved friction control at lower speeds compared with the Reference sample and have overall improved μ-v curves.

TABLE 3

| | Sample 1 0.5 wt % | Sample 2 1 wt % | Reference |
| --- | --- | --- | --- |
| Durability Cycle 1 | 0.122 | 0.120 | 0.128 |
| Durability Cycle 1K | 0.121 | 0.120 | 0.120 |
| Durability Cycle 5K | 0.120 | 0.118 | 0.118 |
| Durability Cycle 10K | 0.121 | 0.117 | 0.116 |
| Comments | Stable throughout test | Stable throughout test | Break-in over initial 1000 cycles followed by decrease |
| Static Friction | 0.135 | 0.113 | 0.163 |
| $\mu_S/\mu_D$ | 1.13 | 0.96 | 1.35 |

The overbased compounds of this invention provide a potent and durable derivative to act as a friction modifier.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A composition comprising an overbased metal salt of an N-substituted 4-carboxypyrrolidin-2-one, wherein the N-substituent comprises a hydrocarbyl group of about 8 to about 24 carbon atoms.

2. The composition of claim 1 wherein the N-substituent comprises a group containing at least one nitrogen atom.

3. The composition of claim 1 wherein the N-substituent comprises a group having one or more amino groups, wherein at least one amino group of said substituent group is further substituted by at least one alkyl group of about 8 to about 20 carbon atoms.

4. The composition of claim 3 wherein at least one amino group in said N-substituent is reacted with dimercaptothiadiazole or a derivative of a dimercaptothiadiazole.

5. The composition of claim 1 wherein said salt has a TBN of about 10 to about 500 mg KOH/g on an oil free basis as measured by ASTM D2896.

6. The composition of claim 1 wherein the metal comprises calcium or magnesium.

7. The composition of claim 1 wherein said salt is carbonated.

8. A lubricant composition comprising an oil of lubricating viscosity and the composition of claim 1.

9. A method of lubricating a mechanical device by supplying thereto the lubricant of claim 8.

10. The method of claim 9 wherein the mechanical device comprises an automatic transmission or manual transmission.

11. The method of claim 9 wherein the mechanical device comprises an engine.

* * * * *